(12) United States Patent
Otis

(10) Patent No.: US 9,333,372 B2
(45) Date of Patent: May 10, 2016

(54) METHODS AND APPARATUS FOR INTERMITTENT STIMULI

(76) Inventor: James Otis, Oakland, CA (US)

(*) Notice: Subject to any disclaimer, the term of this patent is extended or adjusted under 35 U.S.C. 154(b) by 965 days.

(21) Appl. No.: 13/401,841

(22) Filed: Feb. 21, 2012

(65) Prior Publication Data

US 2012/0211013 A1    Aug. 23, 2012

Related U.S. Application Data

(60) Provisional application No. 61/444,766, filed on Feb. 20, 2011.

(51) Int. Cl.
*A61N 5/06* (2006.01)
*A61M 21/02* (2006.01)
*A61N 1/32* (2006.01)
*A61N 1/36* (2006.01)
*A61M 21/00* (2006.01)

(52) U.S. Cl.
CPC ............ *A61N 5/0618* (2013.01); *A61M 21/02* (2013.01); *A61N 1/323* (2013.01); *A61M 2021/0022* (2013.01); *A61M 2021/0027* (2013.01); *A61M 2021/0044* (2013.01); *A61M 2021/0055* (2013.01); *A61M 2021/0072* (2013.01); *A61M 2205/584* (2013.01); *A61N 1/36025* (2013.01)

(58) Field of Classification Search
CPC .............. A61M 21/00; A61M 21/02; A61M 2021/0005; A61M 2021/0016; A61M 2021/0022; A61M 2021/0027; A61M 2021/0044; A61M 2021/0055; A61M 2021/0061; A61M 2021/0072; A61M 2021/0083
See application file for complete search history.

(56) References Cited

U.S. PATENT DOCUMENTS

| | | | | |
|---|---|---|---|---|
| 5,562,718 A | * | 10/1996 | Palermo | A61N 1/36021 607/46 |
| 5,709,645 A | * | 1/1998 | Siever | A61M 21/00 600/26 |
| 6,135,944 A | | 10/2000 | Bowman et al. | |
| 6,167,298 A | * | 12/2000 | Levin | 600/545 |
| 2003/0195383 A1 | * | 10/2003 | Yoon | 600/27 |
| 2010/0056854 A1 | | 3/2010 | Chang | |
| 2010/0324631 A1 | * | 12/2010 | Tass | A61M 21/02 607/88 |

* cited by examiner

Primary Examiner — Charles A Marmor, II
Assistant Examiner — Carrie R Dorna
(74) Attorney, Agent, or Firm — Stephen R. Otis

(57) ABSTRACT

In exemplary implementations of this invention, stimuli are intermittently presented to the left or right side of a user. For example, this invention may comprise a method of presenting stimuli to a bilateral organism, which organism has a left side and a right side, wherein: (a) the stimuli are produced by at least one transducer, (b) the stimuli include an intermittent beat train, and (c) the beat train has a beat frequency that is substantially equal to $7.8 \times (1.618)^n$ Hz, where n is an even integer, which even integer may be negative, zero or positive.

3 Claims, 7 Drawing Sheets

METHODS AND APPARATUS FOR INTERMITTENT STIMULI

RELATED APPLICATIONS

This application claims the benefit of U.S. Provisional Application Ser. No. 61/444,766, filed Feb. 20, 2011, the entire disclosure of which is herein incorporated by reference.

FIELD OF THE TECHNOLOGY

The present invention relates generally to intermittent stimuli.

SUMMARY

In exemplary implementations of this invention, stimuli are intermittently presented to the left or right side of a user. The stimuli may be auditory, visual, haptic, electrical or magnetic. Transducers output intermittent stimuli that are delivered to one or both sides of the body (or one or both visual fields). The intermittent stimuli comprise beat trains.

In some cases, the beat frequencies bear specific mathematical relations to each other. In some cases, some beats in one beat train lag (or lead) some beats in another beat train.

Here are a few definitions and clarifications. As used herein:

A "beat train" is a sequence of beats.

"Beat frequency" is the inverse of beat period. That is, the beat frequency of a beat train is equal to 1/P, where P equals the beat period.

"Beat period" is the period of a beat train. That is, the beat period of a beat train is the time interval from the beginning of one beat to the beginning of the next beat in the beat train. If, within a beat train, that time interval varies, then the beat period of the beat train is the shortest time interval from the beginning of one stressed beat to the beginning of the next stressed beat in the beat train.

A beat train is "intermittent" if it comprises multiple segments, wherein: (a) the beat frequencies in all of the segments are substantially equal, (b) each of the segments comprises at least two stressed beats in consecutive beat periods, and (c) each of the segments is separated from the next segment (if such a next segment exists) by a time interval, which time interval lasts for at least two entire beat periods and does not include any stressed beats.

To illustrate the above definitions, here is a non-limiting example of a beat train: In this example: (a) the beat train has a beat period of 128 ms and a beat frequency of 7.8 Hz; (b) each beat in the beat train has a duration of 13 ms (i.e., each beat lasts for 10% of the beat period), (c) each single beat comprises a signal with a tone (fundamental frequency) of 1552 Hz, (d) some of the beats in the beat train are stressed and some are unstressed, and (e) the unstressed beats have an amplitude of zero.

More definitions may be found in the section entitled "Definitions and Clarifications", below.

Initial experiments indicate that this intermittent stimulation results in a wide range of health benefits. For example, a working prototype of this invention has been used to reduce chronic pain, improve motor coordination and balance, reduce tremors, reduce muscle-tension associated with movement disorders, reduce discomfort associated with irritable bowel syndrome, improve cognitive function for people with learning disabilities, improve attention for people with ADHD, reduce anxiety, and improve mood in people suffering with depression.

The above description of the present invention is just a summary. It is intended only to give a general introduction to some illustrative implementations of this invention. It does not describe all of the details of this invention. This invention may be implemented in many other ways.

BRIEF DESCRIPTION OF THE DRAWINGS

In FIG. 5, the first and second beat trains have beat frequencies of 7.8 Hz and 4.8 Hz, respectively.

In FIG. 6, the first and second beat trains each have a beat period of 207 ms. The first pair of beats of the first beat train and first pair of beats of the second beat train (at 0 seconds, left side of chart) are sounded simultaneously. The second pair of beats of the first beat train and the second pair of beats of the second beat train (at approximately 1.1 seconds on the right side of chart), are sounded so that the beats in the second beat train lag the beats in the first beat train by an amount of time that is substantially equal to 207 ms×0.382.

In FIG. 7, the first and second beat trains each have the same beat frequency and same beat period. However, in different segments of the first and second beat trains, the beats in the first train lead (or lag) the beats in second beat train by different amounts.

The above Figures illustrate some illustrative implementations of this invention, or provide information that relates to those implementations. However, this invention may be implemented in many other ways. The above Figures do not show all of the details of this invention.

DETAILED DESCRIPTION

Figure 1:
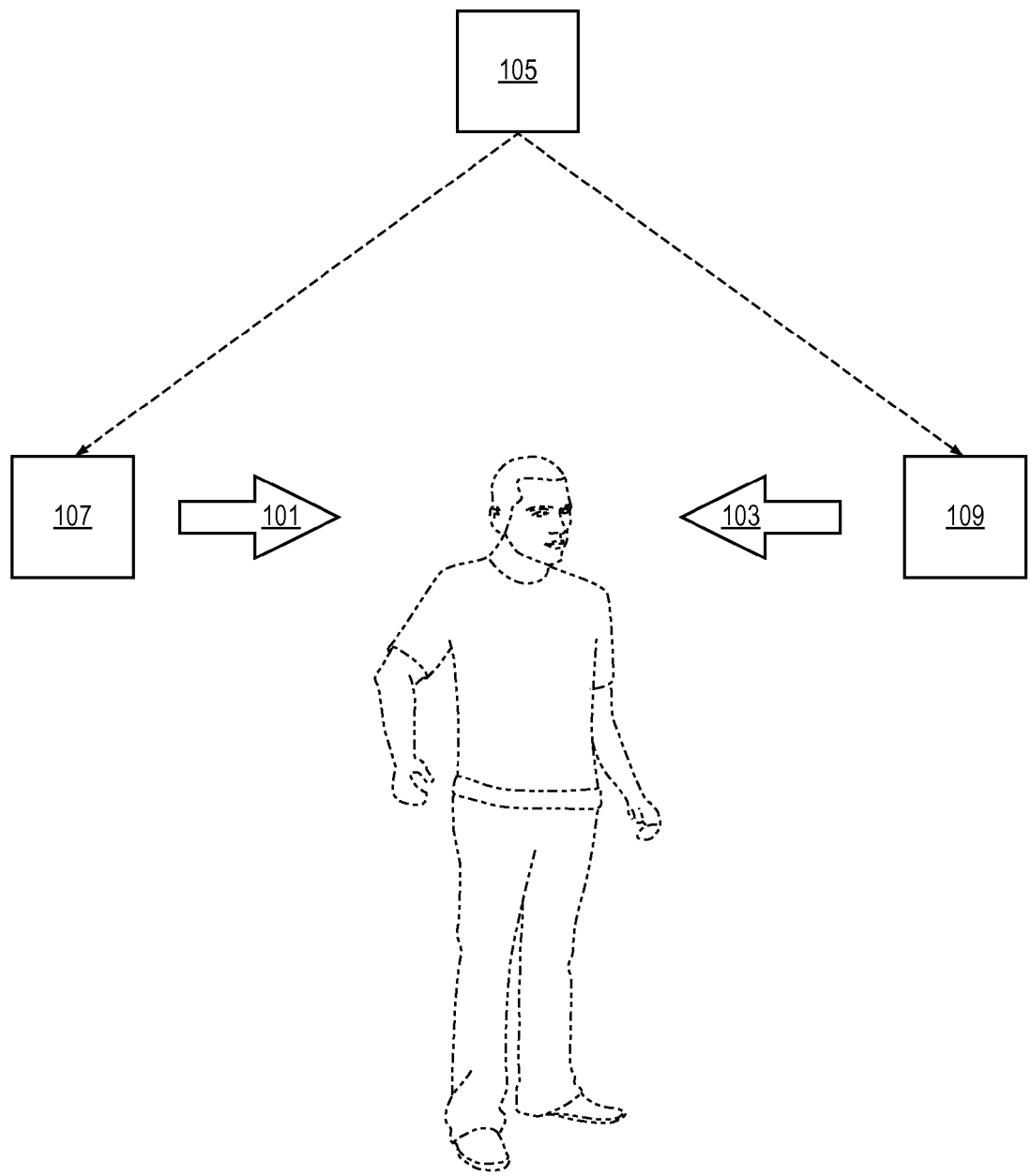
FIG. 1 shows two transducers, one for delivering stimuli to the right side of a person and the other for delivering stimuli to the left side of the person.
Figure 2:
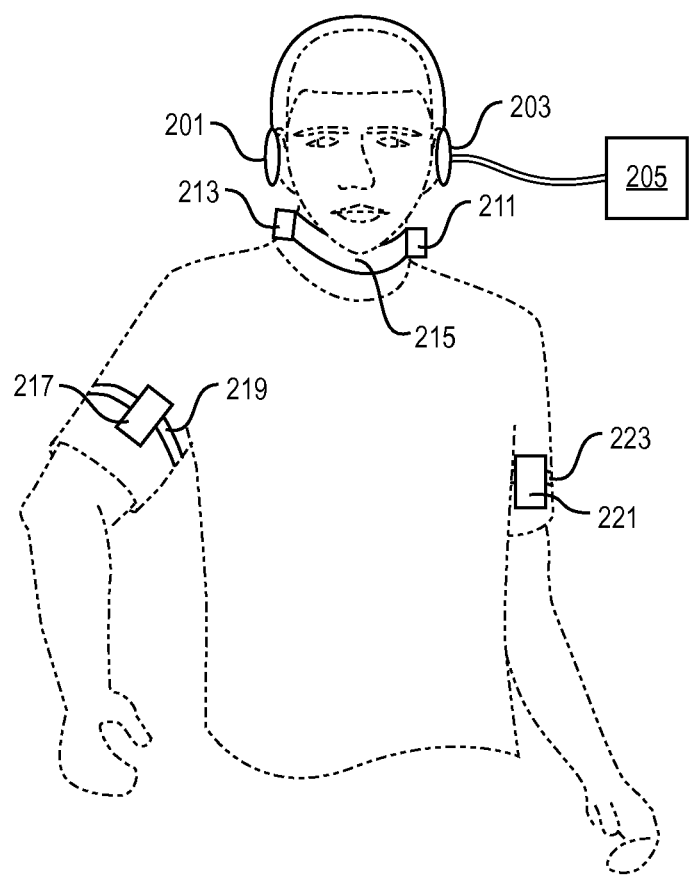
FIG. 2 shows three pairs of transducers for delivering audio, haptic and magnetic stimuli, respectively. In each of the pairs, one transducer delivers stimuli to the right side of the person, and the other transducer delivers stimuli to the left side.
Figure 3:
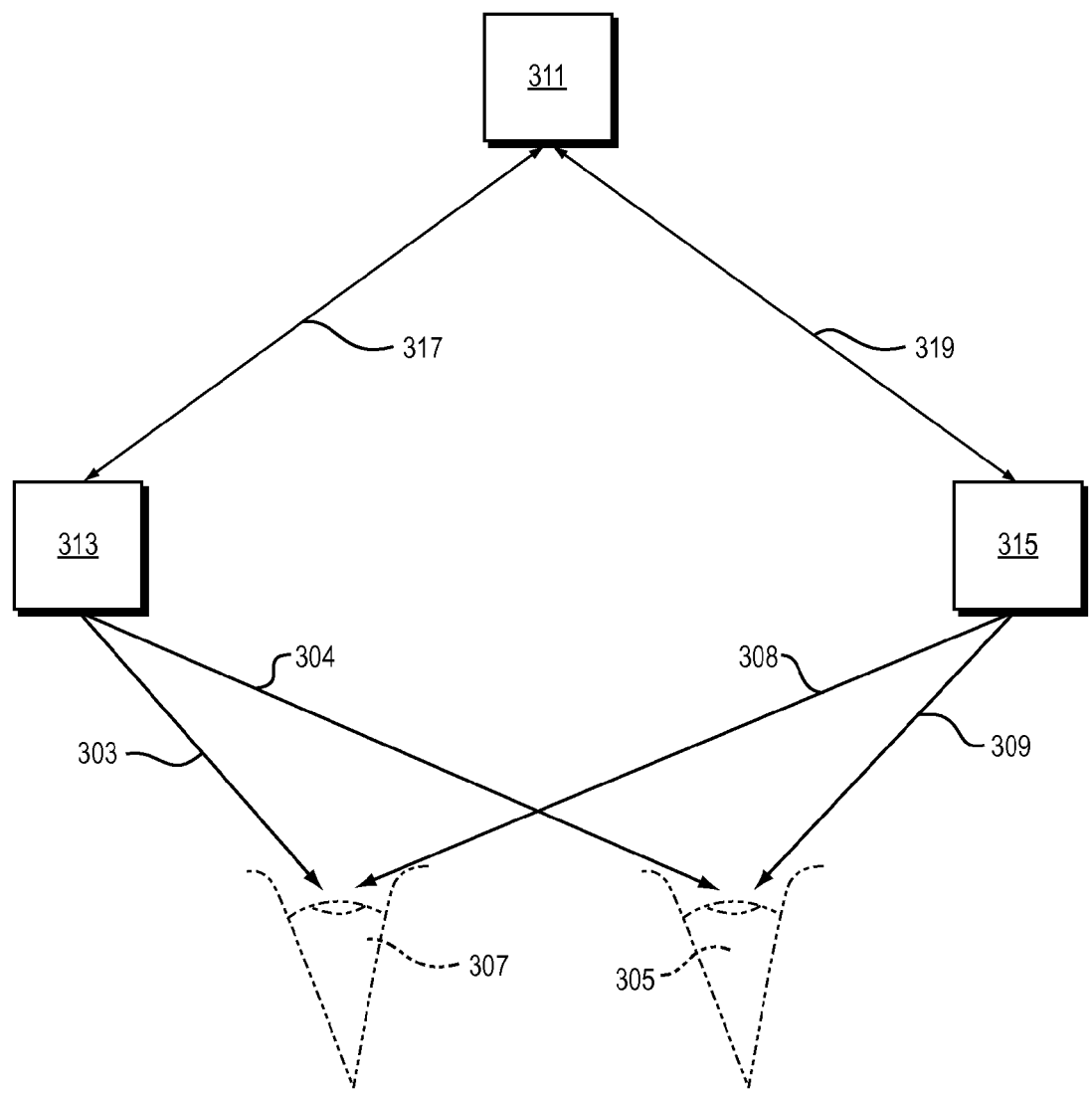
FIG. 3 shows a pair of transducers for delivering visual stimuli. One of the transducers delivers visual stimuli to the right eye, and the other transducer delivers to the left eye.

FIGS. 1, 2 and 3 are diagrams that show three different embodiments of this invention.

In FIG. 1, a transducer 107 presents audio stimuli 101 to the right side of a person, and another transducer 109 presents other audio stimuli 103 to the left side of the person. The transducers 107, 109 are connected to a processor 105 by wired or wireless connections. The processor 105 generates control signals for controlling the transducers 107, 109.

FIG. 2 shows three pairs of transducers for delivering audio, haptic and magnetic stimuli, respectively. In each of the pairs, one transducer delivers stimuli to the right side of the person, and the other transducer delivers stimuli to the left side. Earphones 201 and 203 present audio stimuli to the right and left sides, respectively, of the person. Haptic transducers 211 and 213 are affixed to a necklace (or other object worn around the neck) 215. Haptic transducers 211 and 213 present haptic stimuli to the right and left sides, respectively, of the person. Transducers 217 and 221 are affixed to armbands 219 and 223, respectively. Transducers 217 and 221 present electrical stimuli to the right and left sides, respectively, of the person (or present magnetic stimuli to the right and left sides, respectively, of the person). A processor 205 is connected, directly or indirectly, to each of the transducers, by a wired or wireless connection. The processor 205 generates control signals for controlling the transducers 217, 221.

FIG. 3 shows a pair of transducers 313, 315 for delivering visual stimuli. Light rays 303 and 304 from transducer 313 strike the left eye 307 and right eye 305, respectively. So do light rays 308 and 309 from transducer 315. Visual stimuli produced by transducer 313 are "presented to the left side" (as that phrase is defined herein). Visual stimuli produced by transducer 315 are "presented to the right side" (as that phrase is defined herein). A processor 311 generates control signals for controlling the visual output of transducers 313, 315. The processor is connected to transducers 313, 315 by connections 317, 319. These connections may be wired or wireless.

Figure 4:
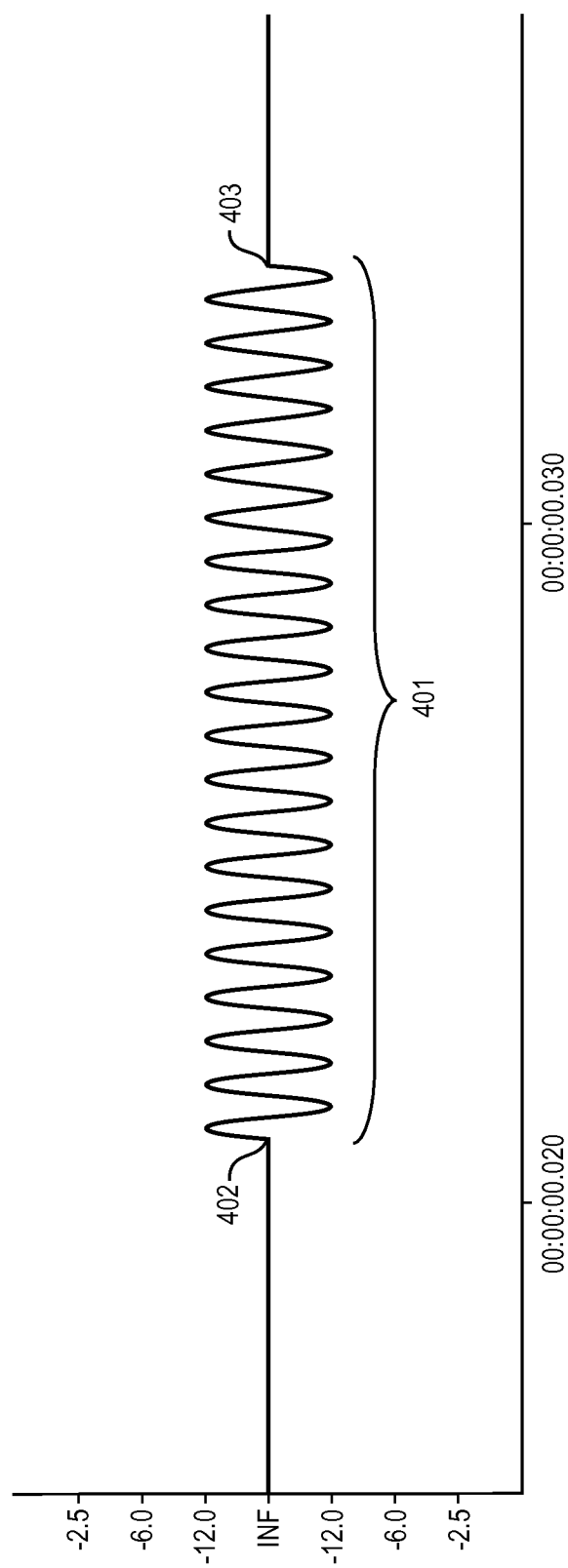
FIG. 4 is a chart of a single beat that lasts for about 13 ms with a tone of about of 1552 Hz.

FIG. 4 is a chart that shows a single beat 401 that lasts for about 13 ms (starting at time 402 and ending at time 403). The single beat 401 has a tone of about of 1552 Hz.

Figure 5:
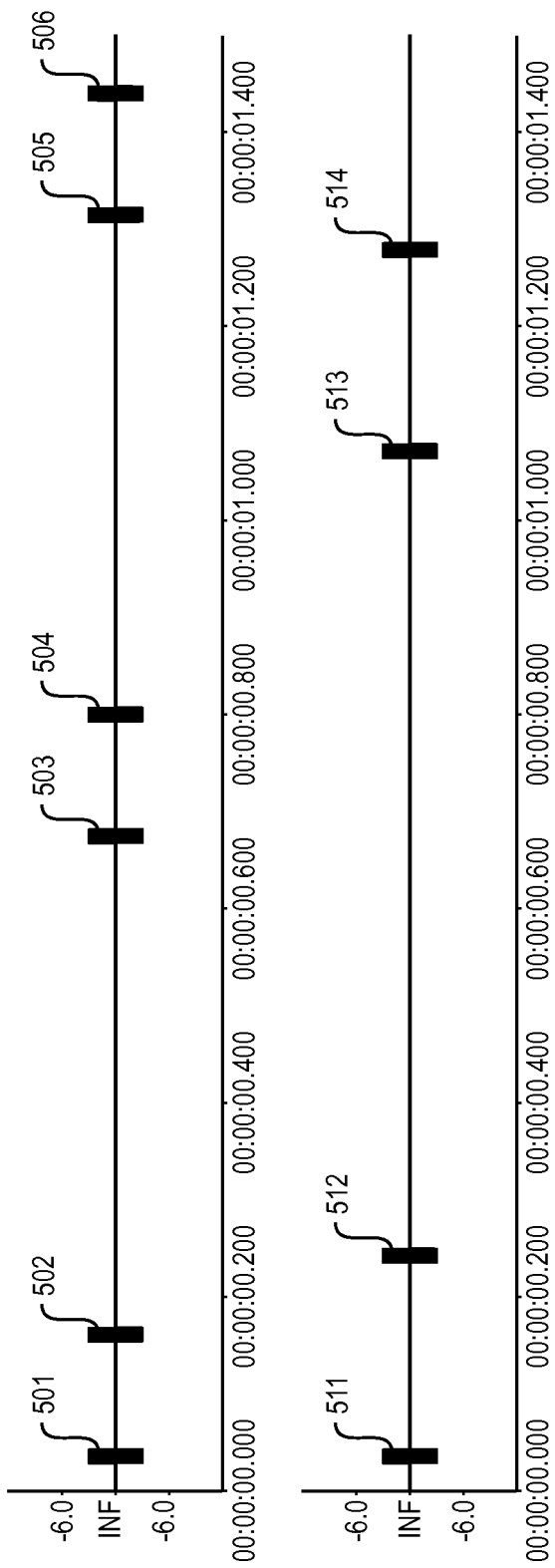
FIGS. 5, 6 and 7 are each a chart of a first beat train (top of chart) and a second beat train (bottom of chart).
Figure 6:
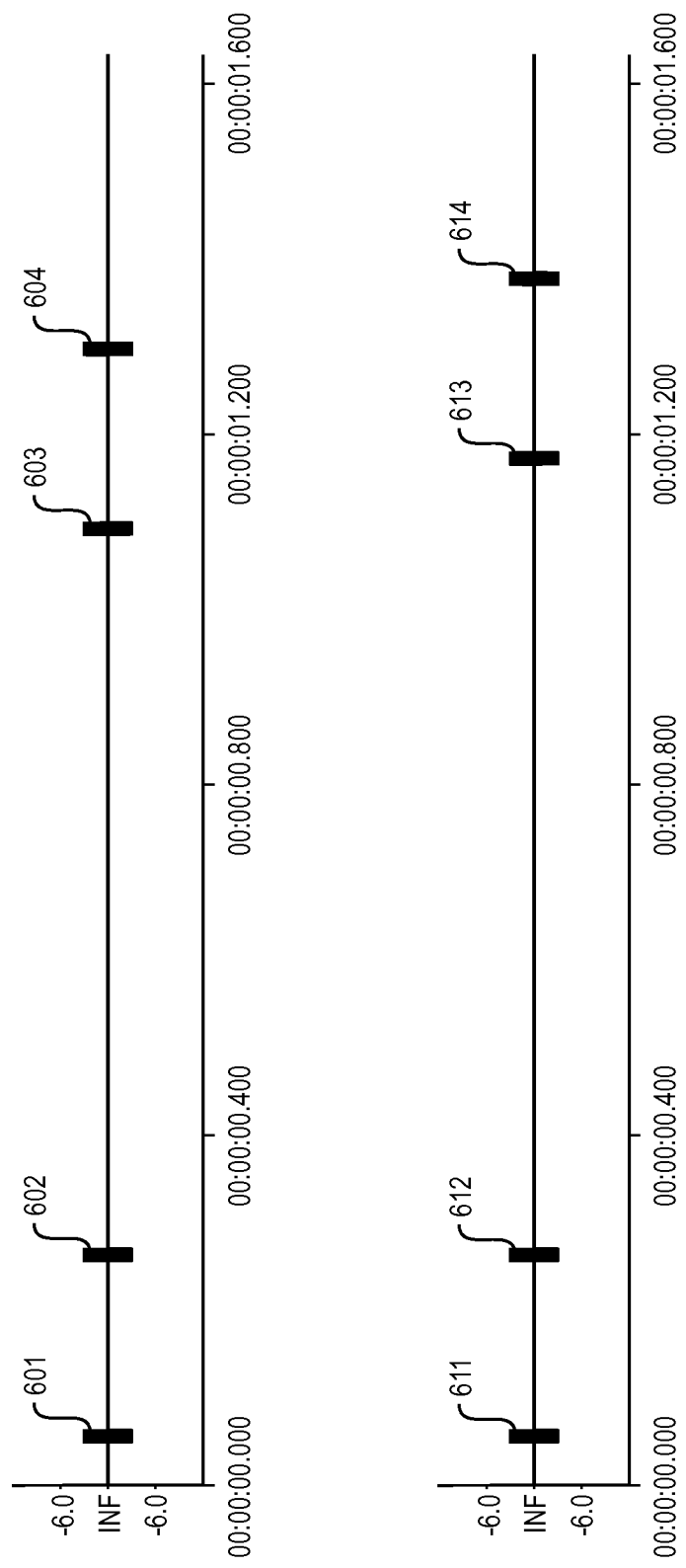
Figure 7:
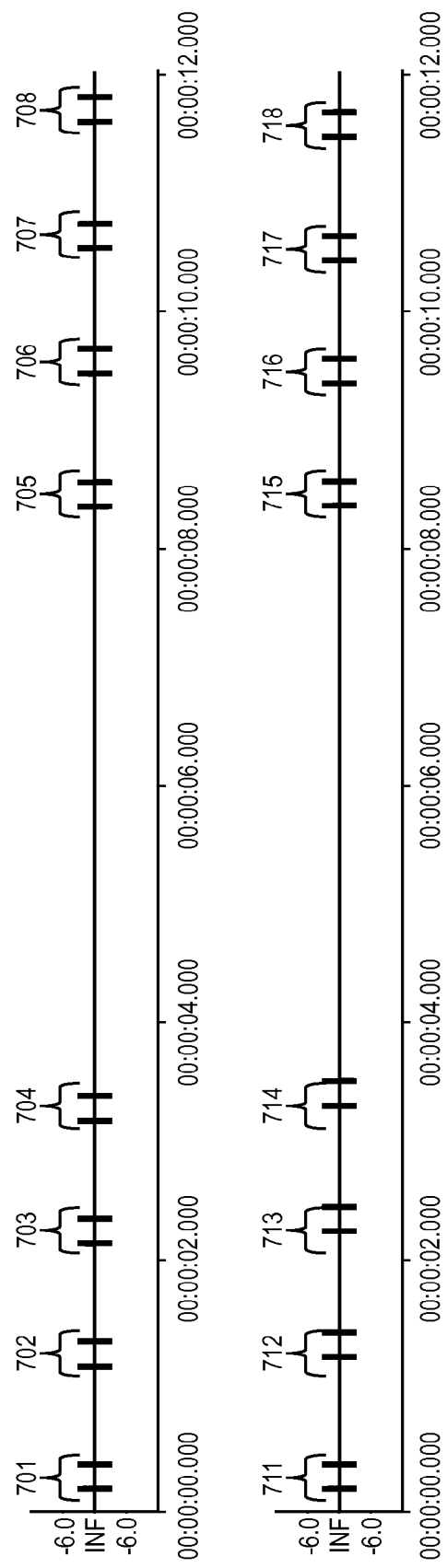

FIGS. 5, 6 and 7 are each a chart of a first beat train (top of chart) and a second beat train (bottom of chart). Both the first and second beat trains are intermittent.

In FIG. 5, the first and second beat trains have beat frequencies of 7.8 Hz and 4.8 Hz, respectively. In the example shown in FIG. 5, the first beat train includes stressed beats 501, 502, 503, 504, 505, 506, and the second beat train includes stressed beats 511, 512, 513, 514, 515, 516.

In FIG. 6, the first and second beat trains each have a beat period of 207 ms. The first pair of stressed beats 601, 602 of the first beat train and first pair of stressed beats of the second beat train 611, 612 (at 0 seconds, left side of chart) are sounded simultaneously. The second pair of stressed beats 603, 604 of the first beat train and the second pair of stressed beats 613, 614 of the second beat train (at approximately 1.1 seconds on the right side of chart), are sounded so that the beats in the second beat train lag the beats in the first beat train by an amount of time that is substantially equal to 207 ms×0.382. In the example shown in FIG. 6, the first beat train includes stressed beats 601, 602, 603, 604, and the second beat train includes stressed beats 611, 612, 613, 614.

In FIG. 7, the first and second beat trains each have the same beat period (the "Example Beat Period"). However, in different segments of the first and second beat trains, the beats in the first beat train lead (or lag) the beats in second beat train by different amounts. In the example shown in FIG. 7, the first beat train includes eight pairs of stressed beats (pairs 701, 702, 703, 704, 705, 706, 707, 708) and the second beat train includes eight pairs of stressed beats (pairs 711, 712, 713, 714, 715, 716, 717, 718).

The beats in pair 711 and pair 701 start at the same times. The beats in pair 712 lag the beats in 702 by an amount of time substantially equal to Example Beat Period times 0.382. The beats in pair 713 lag the beats in 703 by an amount of time substantially equal to Example Beat Period times 0.5. The beats in pair 714 lag the beats in 704 by an amount of time substantially equal to Example Beat Period times 0.618.

The beats in pair 715 and pair 705 start at the same times. The beats in pair 716 lead the beats in 706 by an amount of time substantially equal to Example Beat Period times 0.382. The beats in pair 717 lead the beats in 707 by an amount of time substantially equal to Example Beat Period times 0.5. The beats in pair 718 lead the stressed beats in 708 by an amount of time substantially equal to Example Beat Period times 0.618.

In some implementations of this invention, right and left side stimulation is produced, using one or more beat frequencies. The beat frequencies have a specified ratio "M" to each other, and each beat frequency has a specified time difference between right and left presentation.

In some embodiments, the ratio among the beat frequencies is important, as are the time differences for right and left presentation of beats. The tone frequencies, however, may vary. Many combinations of frequencies meet the specifications of this invention.

In some embodiments: (a) beat trains have beat frequencies that are powers of "M" greater and smaller than 7.8 Hz; (b) stimuli are presented in intermittent beat trains of two or three stressed beats; and (c) stressed beats are presented with different start times on the right and left sides.

In some embodiments, beats on the two sides (right and left) are offset by a time interval substantially equal to the beat period times 0.38.

In some embodiments, stimuli are presented so that the right beat trains lead, the left beat trains lead, or the lead alternates between the right and left sides.

Different types of transducers can be used to present the intermittent stimulation to a user. For example: Stereo headphones or ear buds can be used to deliver intermittent auditory stimulation. LED or other light sources can be used to transmit intermittent visual stimuli to the user. The light sources can be embedded in a helmet or goggles to facilitate separation of stimuli to the right and left visual fields. Vibration devices can be used to transmit intermittent tactile stimuli. They can be held in the hands or attached to the right and left sides of the head, neck, back, feet and other areas of the body. Electromagnets, TENS units, or lasers can be used to deliver intermittent electromagnetic stimulation to the user.

Each row in the table below (Table 1) sets forth a combination of specific values for various parameters (beat frequency, beat period, right-left beat train start time difference, beat duration, and beat tone). These rows are non-limiting examples of combinations that may be used in illustrative embodiments of this invention.

TABLE 1

| Beat Frequency (Hz) | Beat Period (ms) | Right-Left Beat Trains: Start Time Difference (ms) | Beat Duration (ms) | Beat Tone: Example 1 (Hz) | Beat Tone Example 2 (Color) |
|---|---|---|---|---|---|
| 33 | 30 | 12 | 3 | 6574 | |
| 20.4 | 49 | 19 | 5 | 4063 | |
| 12.6 | 79 | 31 | 8 | 2511 | Blue |
| 7.8 | 128 | 49 | 13 | 1552 | Green |
| 4.8 | 207 | 79 | 21 | 959 | Red |
| 3.0 | 336 | 128 | 34 | 593 | |
| 1.8 | 543 | 207 | 54 | 366 | |
| 1.1 | 879 | 336 | 88 | 226 | |
| 0.7 | 1420 | 543 | 142 | 226 | |
| 0.4 | 2300 | 879 | 230 | 140 | |

Two exemplary implementations of this invention are now described, the first ("Implementation A") using auditory stimulation and the second ("Implementation B") using visual stimulation.

Here is an overview of Implementation A: Use the beat frequencies, beat periods, beat durations, right-left start time differences and beat tones specified in Table 1. Use sound editing/generating software to create ten tracks of beats, one track for each of the beat frequencies. Combine the tracks so that all ten are played simultaneously. The user listens with headphones or ear buds that have right-left separation.

Here is more detail regarding Implementation A: In this implementation, use audio editing/generating software (e.g., Sound Forget® software) to perform the following two steps.

Step 1: Create stereo files with right and left channels.

Step 2: Generate a beat train with a beat frequency of 4.8 Hz, as follows: Generate a single beat with a 959 Hz tone and a duration of 207 ms. Mute all but the first 21 ms. This creates a single beat cycle with 21 ms of a 959 Hz tone and 186 ms of silence. Copy the single beat cycle and paste it repeatedly to create an ongoing beat train that has a beat frequency of 4.82 Hz. Each beat cycle in the beat train consists of 21 ms of 959 Hz tone and 186 ms of silence.

Step 3: Make the beat trains intermittent, as follows: Start with eight beat cycles. Mute the last six beat cycles. This creates an intermittent beat train pattern of two sounded beats followed by six silent beats. (That is, the beats in the first two beat cycles are sounded and the beats in the last six beat cycles are silent.)

In steps 4 and 5, create a pair of beat trains, one in the right channel and the other in the left channel, with different start times for right channel and left channel.

Step 4: Create a left-lead sequence (that is, a pair of beat trains, one in the right channel and the other in the left, wherein the beats in the left channel lead the beats in the right channel), as follows: Create a copy, in both the right and left channels, of the sound file that was created in step three. Paste (add) 79 ms of silence to the beginning of the right channel, so that the two sounded beats in the left channel begin 79 ms before the two sounded beats in the right channel.

Step 5: Create a right-lead sequence (that is, a pair of beat trains, one in the right channel and the other in the left, wherein the beats in the right channel lead the beats in the left channel), as follows: Create a copy, in both the right and left channels, of the sound file that was created in step three. Paste (add) 79 ms of silence to the beginning of the left channel, so that the two sounded beats in the right channel begin 79 ms before the two sounded beats in the right channel.

Step 6: Create a pattern of alternating left and right-lead sequences, as follows: Use the left-lead sequence created in Step 4, and the right-lead sequence created in Step 5. Paste them into a new sound file so that a left-channel lead is followed by a right-channel lead in a repeating pattern.

The term "intermittent sequence 1" or "i1 sequence", as used herein, means the pattern of alternating left and right-side sequences created in the first six steps of this first implementation.

Step 7: Create a second level "intermittent sequence 2" or "i2 sequence" from the i1 sequences created in steps 1 through 6, as follows. The basic i2 pattern consists of: two sounded i1 sequences, followed by six muted i1 sequences.

Step 8: Create a third level "intermittent sequence 3" or "i3 sequence" from the i2 sequences created in steps 1 through 7. Start with eight of the i2 sequences created in step 7 and mute the last six. This creates an i3 sequence of two sounded i2 sequences and six muted i2 sequences.

Step 9: Copy the i3 pattern created in step 8 and paste it repeatedly to create a five-minute tract of repeating i3 sequences. In this five minute tract, the beat frequency is 4.8 Hz.

Step 10: Create an intermittent sequence 3 (i3 sequence) for beat frequencies 7.8, 12.6, 20.4, and 33 Hz by following steps 1-10 as specified above, with the following modification: Use the appropriate beat period, beat duration, right-left start time difference, and beat tone for each of the 7.8, 12.6, 20.4 and 33 Hz beat frequencies as determined from Table 1.

Step 11: Create an intermittent sequence 2 (i2 sequence) for the 0.7, 1.1, 1.8, and 3 Hz beat frequencies following steps 1 through 8, with the following modification: Use the appropriate beat period, beat duration, right-left start time difference, and beat tones for each of the 0.7, 1.1, 1.8, and 3 Hz beat frequencies as determined from Table 1. For these beat frequencies (0.7, 1.1, 1.8, and 3 Hz), stop at intermittent pattern 2 (i2) and do not proceed to i3.

Step 12: Create intermittent sequence 1 (i1 sequence) for the 0.4 Hz beat frequency following steps 1 through 7 used to create the 4.8, 7.8, 12.6, 20.4, and 33 beat frequencies, with the following modification: Use the appropriate beat period, beat duration, right-left start time difference, and beat tone for the 0.4 beat frequency as determined from Table 1. For the 0.4 Hz beat frequency, stop at intermittent sequence 1 (i1 sequence) and do not proceed to i2 or i3.

Step 13: At this point ten five-minute tracks have been created, one for each of the beat frequencies 0.4, 0.7, 1.1, 1.8, 3, 4.8, 7.8, 12.6, 20.4, and 33 Hz. Mix the ten tracks to create a single five-minute track that combines all ten intermittent beat sequences.

Step 14: The user listens to this combination of stimuli with headphones, ear buds, or some other arrangement that preserves right-left separation.

Implementation B employs visual stimulation. Here is an overview of this Implementation B: Use beat frequencies, beat periods, beat durations, right-left start time differences and beat tones (color) from Table 1. Rather than use intermittent audio beats with different beat tones, use intermittent beats of light of different colors. The signal transducers in this example are 6 lights with tinted filters, two each with blue, green and red. A group of three lights (blue, green, red) is mounted on each side of a helmet worn by the user, so that one group stimulates the right visual field and the other group stimulates the left visual field.

Here is more detail regarding Implementation B. In this implementation, perform the following three steps.

Step 1: program software to turn each light on and off with beat frequencies, beat durations, and right-left start time differences specified in table 1.

Step 2: Create three intermittent sequences, one for each light, using the same approach as in steps 1-8, with the following modifications: The beat duration, the timing and the method of right and left presentation all remain the same. Light stimulation is used instead of auditory stimulation. For example, use red light flashed for 21 ms every 207 ms instead of beat tone 959 Hz sounded for 21 ms every 207 ms, etc.

Step 3: Combine the three intermittent sequences created in steps 1 and 2 and present them simultaneously to the user in a way that maintains differentiation for stimuli presented to the right and left sides of the user.

In some implementations of this invention: Present Stimuli to the user for 2-15 minutes two or more times a day. Present the stimuli in an intermittent fashion. Continuous presentation of stimuli in these frequency ranges causes neurological fatigue that diminishes the efficacy of the technology. Use higher levels of intermittent iteration for higher frequency beat frequencies. For example, use i1 sequences for beat frequency 0.4, and i3 sequences for beat frequencies of 4.8 and higher. Use greater sound volume for low frequency auditory stimulation and less sound volume for the higher beat frequencies. Use a group of beat frequencies that includes 7.8 Hz.

A processor (e.g., 105, 205, 311) is shown in each of FIGS. 1, 3, and 3. That processor may comprise one or more computer processors, at least some of which may be remote from others or from the input device or optical apparatus. The one or more processors may be connected wirelessly, or by wired connection, or by some combination of the wireless and wired connections.

In some implementations, the processor either retrieves an audio file (or other content file) from memory or retrieves it from another computer (e.g., from a host server via the Internet). Alternately, the processor generates an audio file (or other content file, for example, content for haptic, visual stimulation).

In exemplary implementations of this invention, repeated exposure facilitates improved physical, mental and emotional health.

DEFINITIONS AND CLARIFICATIONS

The following terms are defined in the "Summary" section, above:
(a) "beat train"
(b) "beat frequency"
(c) "beat period", and
(d) "intermittent"

Here are some more definitions and clarifications. As used herein:

The terms "a" and "an", when modifying a noun, do not imply that only one of the noun exists. For example, if a set includes "a" red member, then the set includes one or more red members.

The term "include" shall be construed broadly, as if followed by "without limitation".

A "left beat train" is a beat train presented to the left side of a bilateral organism.

The term "or" is an inclusive disjunctive. For example "A or B" is true if A is true, or B is true, or both A or B are true.

An "organism" includes a human or animal.

"Phi" or "ϕ" means the golden ratio, an irrational number that is equal to $$\frac{1+\sqrt{5}}{2} \approx 1.61803.$$

A percentage difference between two values is calculated as follows: If x=y, then the percentage difference is zero. If x≠y, call the larger of the two values x and the smaller of the two values y. Then the percentage difference between the two values is equal to $|(x-y)/x| \times 100$.

A stimulus (other than a visual stimulus) is "presented to both sides" if the amplitude of the stimulus on the left and right sides, respectively, differs by less than 50%.

A stimulus (other than a visual stimulus) is "presented to the left side" of an organism if (a) the amplitude of the stimulus on the left side is greater than the amplitude of the stimulus on the right side, and (b) the amplitude of the stimulus on the left side and the amplitude of the stimulus on the right side differ by at least 50%.

A stimulus (other than a visual stimulus) is "presented to the right side" of an organism if (a) the amplitude of the stimulus on the right side is greater than the amplitude of the stimulus on the left side, and (b) the amplitude of the stimulus on the left side and the amplitude of the stimulus on the right side differ by at least 50%.

A visual stimulus is "presented to both sides" of an organism if the visual stimulus comprises incident light rays and the maximum angle of impact (as defined herein) of the incident light rays on both eyes of the organism is less than 10 degrees. For example, if the maximum angle of impact is 9 degrees for the right eye and 7 degrees for the left eye, then the visual stimulus is "presented to both sides" of the organism.

A visual stimulus is "presented to the left side" of an organism if the incident light rays that form the visual stimulus approach the organism from the left and the maximum angle of impact of the incident light rays on either eye of the organism equals or exceeds 10 degrees. For example, if the incident light rays approach the organism from the left and the maximum angle of impact is 15 degrees for the right eye and 8 degrees for the left eye, then the visual stimulus is presented from the left side. Also, for example, if the incident light rays approach the organism from the left, but strike only the right eye and not the left eye, and the maximum angle of impact is 30 degrees for the right eye, then the visual stimulus is "presented to the left side".

A visual stimulus is "presented to the right side" of an organism if the incident light rays that form the visual stimulus approach the organism from the right and the maximum angle of impact of the incident light rays on either eye of the organism equals or exceeds 10 degrees. For example, if the incident light rays approach the organism from the right and the maximum angle of impact is 8 degrees for the right eye and 15 degrees for the left eye, then the visual stimulus is presented from the right side. Also, for example, if the incident light rays approach the organism from the right, but strike only the left eye and not the right eye, and the maximum angle of impact is 20 degrees for the left eye, then the visual stimulus is "presented to the right side".

For purposes of the definitions of a visual stimulus "presented to both sides", or "presented to the left side", or "presented to the right side", of an organism: (A) "incident light rays" are light rays that form the visual stimulus and that strike an eye of the organism; (B) the "angle of impact" of an incident light ray is the angle between (i) the sagittal plane of the organism and (ii) the direction of travel of the incident light ray immediately before it strikes an eye, (C) to approach the organism "from the left" means to approach from a point that is to the left of the organism's sagittal plane, and (D) to approach the organism "from the right" means to approach from a point that is to the right of the organism's sagittal plane.

A "processor" means one or more computer processors, at least some of which processors may be spatially remote from other processors.

A "right beat train" is a beat train presented to the right side of a bilateral organism.

A "stressed" beat has a greater amplitude than a beat that is not stressed (or that is "unstressed").

"Substantially" has the following meaning Any two values x and y are "substantially equal" if they differ by 5% or less. Any two values x and y "differ substantially" if they differ by more than 5%. A variable v is "substantially constant" if the highest value reached by v and lowest value reached by v are substantially equal. A variable v "varies substantially" if it is not substantially constant.

"User" means any human or other bilateral organism exposed to beat trains. For example, a user may be a patient or a healthy person who uses such exposure to improve physiologic or neurologic functioning.

The "tone" of a beat means the fundamental frequency of the stimulus that comprises the beat. For example, a single beat may have a duration of 13 ms, and during that single beat, the beat may have a tone of 2511 Hz. The "tone" of a beat is not the same as the beat frequency.

VARIATIONS

This invention may be implemented in many ways. Here are some more non-limiting examples:

Vary the beat frequencies. For example use beat frequencies that are powers of an arbitrary number times 6 Hz, 8 Hz, or 10 Hz. instead powers of phi times 7.8 Hz.

Use any single beat frequency to create an intermittent pattern of stimulation.

Use beats with no side-to-side difference in beat onset, or beats with differences of side-to-side onset such that the right side always leads, or the left side always leads.

Use different combinations of beat frequencies; for example 0.7 Hz and 1.1 Hz, or 4.8 Hz and 12.6 Hz.

Use a different combination of stressed (e.g., sounded) and unstressed (e.g., muted) beats.

Use a two-sounded-three-muted or two-sounded-eleven-muted pattern instead of a two-sounded-six-muted pattern.

Use a different level of intermittent beat pattern. For example, use i2 or i4 instead of i3, etc.

Use a different tone for an auditory beat.

Use a different color (tone) for a visual beat.

Combine stimulation modalities. For example, use haptic stimulation to deliver 0.4, 0.7, and 1.1 Hz beat trains, auditory stimulation to deliver 1.8, 3.0 and 4.8 Hz beat trains, and visual stimulation to deliver 7.8 and 12.6 Hz beat trains.

Use a different beat duration. For example use 10 ms, 30 ms, or 50 ms beat durations instead of 21 ms beat durations to produce a 4.82 Hz beat frequency.

Combine the intermittent beat stimulation with a variety of physical and mental activities. Have user focus their attention on the visual, tactile or auditory stimulation, or have the user do other activities such as physical or mental exercises while using the technology.

Present stimuli subliminally instead of liminally. For example, use low intensity TENS to deliver subliminal electromagnetic beats or mask auditory beats with pink noise or nature sounds to deliver subliminal auditory beats.

Use different beat frequencies or intermittent patterns during a single therapeutic session, so that different stimulation is used during different portions of the therapeutic session.

Incorporate these ratios into therapeutic games. For example: (a) the player is presented with three beat frequencies that have frequency ratios equal to either the cube root of phi or the square root of phi; (b) the player attempts provide input to the system in synchrony with one of the beat frequencies; (c) the player receives feedback about the temporal relation of player input compared to the stimulus presentation; (d) feedback includes information about lead or lag of user input relative to beat stimuli; (e) the player attempts to decrease lead and/or lag times and earn a higher score.

Each of the following are examples of parameters that may vary, depending on the particular implementation: (a) beat frequency; (b) type of stimuli (e.g., sound, light, haptic, magnetic or electrical), (c) tone, (d) beat length, (e) type of transducer, and (f) where the stimuli are delivered (as long as the proper left-right orientation is achieved), e.g., whether tactile stimuli delivered on the feet or on the hands).

In exemplary implementations of this invention, the mathematical ratios of the outputted beat frequencies are not exact, but are subject to insubstantial deviations. These deviations may arise, for example, from rounding error, distortions caused by signal processing hardware or software, or inaccurate rendering by transducers.

This invention may be implemented as a method for improving health (or relieving symptoms, treating disease, or improving neurological or physiological functioning) by exposing a user to intermittent stimuli.

This invention may be implemented as a medium on which auditory, visual, haptic or other content is stored in a nontransitory computer readable form, which content is data representative of intermittent stimuli. Such medium may, for example, be a CD, DVD, flash memory, phonograph record or any other medium for storing digital or analog data.

This invention may be implemented as a medium on which a software program is stored in a nontransitory computer readable form, which software program comprises instructions for a processor to generate signals for directly or indirectly causing transducers to output intermittent stimuli. For example, such signals may comprise analog or digital signals representative of auditory, visual or haptic stimuli. Or, for example, such signals may comprise control signals for triggering the playback of auditory, visual or haptic samples from memory. Such medium may, for example, be a CD, DVD or flash memory.

This invention may be implemented as a system, which system comprises a plurality of transducers, one or more memory devices, and one or more processors for generating control signals for controlling transducers to produce intermittent beat trains. Such a system may comprise, for example, a handheld or portable electronic device (e.g., a smart phone, portable media player, tablet computer or laptop computer), CD player, DVD player, personal computer or other internet streaming device, in each case with internal or external transducers.

This invention may be implemented as a method of presenting stimuli to a bilateral organism, which organism has a left side and a right side, wherein: (a) the stimuli may be produced by at least one transducer, (b) the stimuli may include an intermittent beat train, and (c), the beat train has a beat frequency that is substantially equal to $7.8 \times (1.618)^n$ Hz, where n is an even integer, which even integer may be negative, zero or positive. Furthermore: (1) n may be equal to 1; (2) n may be greater than or equal to −10 and less than or equal to 10; and (3) in some instantiations, during all of a time interval that lasts for at least two entire successive beat periods and that includes at least two sounded beats, the beat train is either presented to the right side (but not to the left side) of the organism, or presented to the left side (but not to the right side) of the organism.

This invention may be implemented as a method of presenting stimuli to a bilateral organism, which organism has a left side and a right side, wherein (a) the stimuli are produced by at least one transducer, (b) the stimuli comprise a first beat train and a second beat train, (c) the first and second beat trains are each intermittent, (d) the first beat train has a first beat frequency and the second beat train has a second beat frequency, and (e) the second beat frequency is either substantially equal to the first beat frequency times 1.618 or substantially equal to the first beat frequency times 0.618. Furthermore: (1) the first beat frequency may be substantially equal to 7.8 Hz; (2) the first beat frequency may be substantially equal to $7.8 \times (1.618)^n$ Hz, where n is an even integer, which even integer may be negative, zero or positive, (3) in some instantiations, during all of a time interval that lasts for at least two entire successive beat periods and that includes at least two sounded beats, either (i) the first beat train is presented to the right side (but not to the left side) and the second beat train is presented to the left side (but not to the right side), (ii) the first beat train is presented to the left side (but not to the right side) and the second beat train is presented to the right side (but not to the left side), (iii) both the first and second beat trains are presented to the right side and neither the first nor the second beat trains are presented to the left side, or (iv) both the first and second beat trains are presented to the left side and neither the first nor the second beat trains are presented to the right side, (4) at least some of the stimuli may be audio, (5) at least some of the stimuli may be visual, and (6) at least some of the stimuli may be haptic.

This invention may be implemented as a method of presenting stimuli to a bilateral organism, which organism has a left side and a right side, wherein: (a) the stimuli are produced by at least one transducer, (b) the stimuli comprise a first intermittent beat train and a second intermittent beat train, (c) the first beat train has a first beat frequency and a first beat period and the second beat train has a second beat frequency and a second beat period, (d) the first and second beat frequencies are substantially equal, and (e) during all of a time interval that lasts for at least two entire successive beat periods and that includes at least two sounded beats, beats in the first beat train lag beats in the second beat train by a time interval that is substantially equal to the first beat period times 0.382. In some instantiations, during all of the time interval, either (i) the first beat train is presented to the right side (but not to the left side) and the second beat train is presented to the left side (but not to the right side), (ii) the first beat train is presented to the left side (but not to the right side) and the second beat train is presented to the right side (but not to the left side), (iii) both the first and second beat trains are presented to the right side and neither the first nor the second beat trains are presented to the left side, or (iv) both the first and second beat trains are presented to the left side and neither the first nor the second beat trains are presented to the right side. Furthermore: (1) the first and second beat frequencies may be substantially equal to 7.8 Hz; (2) the stimuli may further comprise a third beat train and fourth beat train, which third and fourth beat trains are each intermittent, have a third beat frequency and a fourth beat frequency, respectively, and have a third beat period and a fourth beat period, respectively, the third and fourth beat frequencies being each substantially equal to the first beat frequency times 0.618, and during all of the time interval, beats in the third beat train may lag beats in the fourth beat train by a second time interval that is substantially equal to the third beat period times 0.382; (3) the stimuli may further comprise a fifth beat train and sixth beat train, which fifth and sixth beat trains are each intermittent, have a fifth beat frequency and a sixth beat frequency, respectively, and have a fifth beat period and a sixth beat period, respectively, the fifth and sixth beat frequencies being each substantially equal to the third beat frequency times 0.618, and during all of the time interval, beats in the fifth beat train lag beats in the sixth beat train by a third time interval that is substantially equal to the fifth beat period times 0.382; (4) the first and second beat frequencies may each be substantially equal to 7.8 Hz, the third and fourth beat frequencies may each be substantially equal to 4.8 Hz, and the fifth and sixth beat frequencies may each be substantially equal to 3.0 Hz.

This invention may be implemented as a method of presenting stimuli to a bilateral organism, which organism has a left side and a right side, wherein (a) the stimuli are produced by transducers, (b) the stimuli comprise a first intermittent beat train and a second intermittent beat train, (c) the first beat train has a first beat frequency and a first beat period and the second beat train has a second beat frequency and a second beat period, (d) the first and second beat frequencies are substantially equal, and (e) during all of a time interval that lasts for at least two entire successive beat periods and that includes at least two sounded beats, beats in the first beat train lag beats in the second beat train by a time interval that is substantially equal to the first beat period times 0.618. In some instantiations, during all of the time interval, either (i) the first beat train is presented to the right side (but not to the left side) and the second beat train is presented to the left side (but not to the right side), (ii) the first beat train is presented to the left side (but not to the right side) and the second beat train is presented to the right side (but not to the left side), (iii) both the first and second beat trains are presented to the right side and neither the first nor the second beat trains are presented to the left side, or (iv) both the first and second beat trains are presented to the left side and neither the first nor the second beat trains are presented to the right side.

This invention may be implemented as a tangible computer readable storage medium having instructions encoded thereon for instructing a processor to generate signals for controlling at least one transducer to present stimuli to a bilateral organism, which bilateral organism has a right side and a left side, wherein: (a) the stimuli comprise a first beat train and a second beat train, (b) the first and second beat trains are each intermittent, (c) the first beat train has a first beat frequency and the second beat train has a second beat frequency, and (d) the second beat frequency is either substantially equal to the first beat frequency×1.618 or substantially equal to the first beat frequency×0.618.

CONCLUSION

It is to be understood that the methods and apparatus which have been described above are merely illustrative applications of the principles of the invention. Numerous modifications may be made by those skilled in the art without departing from the scope of the invention. The scope of the invention is not to be limited except by the claims that follow.

What is claimed:

1. A method of presenting stimuli to a bilateral organism, which organism has a left side and a right side, wherein:
   (a) the stimuli are produced by at least one transducer;
   (b) the stimuli comprise a first intermittent beat train and a second intermittent beat train;
   (c) the first beat train has a first beat frequency and a first beat period and the second beat train has a second beat frequency and a second beat period;
   (d) the first and second beat frequencies are substantially equal;
   (e) during all of a time interval that lasts for at least two entire successive beat periods and that includes at least two sounded beats, beats in the first beat train lag beats in the second beat train by a time interval that is substantially equal to the first beat period times 0.382;
   (f) the stimuli further comprise a third beat train and fourth beat train, which third and fourth beat trains are each intermittent, have a third beat frequency and a fourth beat frequency, respectively, and have a third beat period and a fourth beat period, respectively, the third and fourth beat frequencies being each substantially equal to the first beat frequency times 0.618; and
   (g) during all of the time interval, beats in the third beat train lag beats in the fourth beat train by a second time interval that is substantially equal to the third beat period times 0.382.

2. The method of claim 1, wherein
   the stimuli further comprise a fifth beat train and sixth beat train, which fifth and sixth beat trains are each intermittent, have a fifth beat frequency and a sixth beat frequency, respectively, and have a fifth beat period and a sixth beat period, respectively, the fifth and sixth beat frequencies being each substantially equal to the third beat frequency times 0.618, and
   during all of the time interval, beats in the fifth beat train lag beats in the sixth beat train by a third time interval that is substantially equal to the fifth beat period times 0.382.

3. The method of claim 2, wherein the first and second beat frequencies are each substantially equal to 7.8 Hz, the third and fourth beat frequencies are each substantially equal to 4.8 Hz, and the fifth and sixth beat frequencies are each substantially equal to 3.0 Hz.

* * * * *